(12) United States Patent
Tillyer et al.

(10) Patent No.: US 6,281,391 B1
(45) Date of Patent: Aug. 28, 2001

(54) SYNTHESIS OF METHYLTHIOPHENYL HYDROXYKETONES

(75) Inventors: Richard D. Tillyer, Westfield; Ian W. Davies, Princeton; Robert D. Larsen, Bridgewater, all of NJ (US); Xin Wang, Kirkland; Paul O'Shea, Montreal, both of (CA); Anthony On-Ping King, Hillsborough, NJ (US); Dalian Zhao, Fanwood, NJ (US); Cheng Y. Chen, Colonia, NJ (US); Edward J. J. Grabowski, Westfield, NJ (US)

(73) Assignees: Merck & Co., Inc., Rahway, NJ (US); Merck Frosst Canada & Co., Kirkland (CA)

( * ) Notice: Subject to any disclaimer, the term of this patent is extended or adjusted under 35 U.S.C. 154(b) by 0 days.

(21) Appl. No.: 09/427,413

(22) Filed: Oct. 27, 1999

Related U.S. Application Data

(60) Provisional application No. 60/105,830, filed on Oct. 27, 1998.

(51) Int. Cl.[7] .................................................. C07C 319/20
(52) U.S. Cl. .................. 568/43; 568/42; 568/67
(58) Field of Search ................ 568/39, 42, 43, 568/67; 548/530, 540

(56) References Cited

U.S. PATENT DOCUMENTS

| 5,474,995 | * 12/1995 | Ducharme et al. ................ 514/241 |
|---|---|---|
| 5,663,195 | 9/1997 | Scolnik . |
| 5,840,746 | 11/1998 | Ducharme et al. . |
| 6,020,343 | * 2/2000 | Belley et al. ........................ 514/309 |

FOREIGN PATENT DOCUMENTS

| 3002 | * 7/1979 | (EP) . |
|---|---|---|
| 96/19469 | * 6/1996 | (WO) . |
| 98/41516 | * 9/1998 | (WO) . |

OTHER PUBLICATIONS

CA:127:34112 abst of WO/9716435, May 1997.*

* cited by examiner

*Primary Examiner*—Jean F Vollano
(74) *Attorney, Agent, or Firm*—Richard C. Billups; David L. Rose

(57) ABSTRACT

This invention encompasses a novel process for synthesizing compounds represented by formula A:

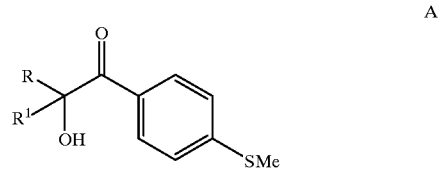

These compounds are intermediates useful in the preparation of certain agents that are selective COX-2 inhibitors.

29 Claims, No Drawings

SYNTHESIS OF METHYLTHIOPHENYL HYDROXYKETONES

CROSS REFERENCE TO RELATED APPLICATIONS

This application is a non-provisional application related to U.S. application Ser. No. 60/105,830, filed on Oct. 27, 1998 priority of which is claimed hereunder.

BACKGROUND OF THE INVENTION

This application is directed to an improved process for making methythiophenyl hydroxyketones such as (S)-2-hydroxy-2-methyl-1 -(4-methylthiophenyl)butan-1-one. These compounds are intermediates useful in the preparation of certain compounds that selectively inhibit cyclooxygenase-2 (COX-2). Compounds having COX-2 selectivity, for example, are found in WO 97/14691 filed on Oct. 9, 1996 and published on Apr. 24, 1997.

Non-steroidal, antiinflammatory drugs exert most of their antiinflammatory, analgesic and antipyretic activity and inhibit hormone-induced uterine contractions and certain types of cancer growth through inhibition of prostaglandin G/H synthase, also known as cyclooxygenase. Initially, only one form of cyclooxygenase was known, this corresponding to cyclooxygenase-1 (COX-1) or the constitutive enzyme, as originally identified in bovine seminal vesicles. More recently the gene for a second inducible form of cyclooxygenase, COX-2 has been cloned, sequenced and characterized initially from chicken, murine and human sources. This enzyme is distinct from the COX-1 which has been cloned, sequenced and characterized from various sources including the sheep, the mouse and man. The second form of cyclooxygenase, COX-2, is rapidly and readily inducible by a number of agents including mitogens, endotoxin, hormones, cytokines and growth factors. As prostaglandins have both physiological and pathological roles, we have concluded that the constitutive enzyme, COX-1, is responsible, in large part, for endogenous basal release of prostaglandins and hence is important in their physiological functions such as the maintenance of gastrointestinal integrity and renal blood flow. In contrast, we have concluded that the inducible form, COX-2, is mainly responsible for the pathological effects of prostaglandins where rapid induction of the enzyme would occur in response to such agents as inflammatory agents, hormones, growth factors, and cytokines. Thus, a selective inhibitor of COX-2 will have similar antiinflammatory, antipyretic and analgesic properties to a non-steroidal antiinflammatory drug, and in addition would inhibit hormone-induced uterine contractions and have potential anti-cancer effects, but will have a diminished ability to induce some of the mechanism-based side effects. In particular, such a compound should have a reduced potential for gastrointestinal toxicity, a reduced potential for renal side effects, a reduced effect on bleeding times and possibly a lessened ability to induce asthma attacks in aspirin-sensitive asthmatic subjects.

Furthermore, such a compound will also inhibit prostanoid-induced smooth muscle contraction by preventing the synthesis of contractile prostanoids and hence may be of use in the treatment of dysmenorrhea, premature labour, asthma and eosinophil related disorders. It will also be of use in the treatment of Alzheimer's disease, for decreasing bone loss particularly in postmenopausal women (i.e. treatment of osteoporosis) and for the treatment of glaucoma.

A brief description of the potential utility of selective COX-2 inhibitors is given in an article by John Vane, *Nature*, Vol. 367, pp. 215–216, 1994, and in an article in *Drug News and Perspectives*, Vol. 7, pp. 501–512, 1994.

SUMMARY OF THE INVENTION

This invention encompasses a novel process for synthesizing compounds represented by formula A:

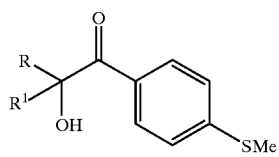

wherein R and $R^1$ are $C_{1-6}$alkyl, comprising reacting a compound of formula B:

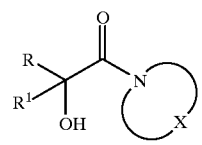

wherein the group:

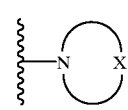

represents a 5 or 6-membered non-aromatic ring wherein X is selected from the group consisting of: C, N, O and S, with a lithiating agent and a compound of formula C:

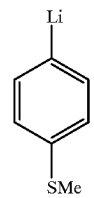

in a substantially non-reactive solvent at reduced temperature to produce a compound of formula A.

These compounds are intermediates useful in the preparation of certain agents which are selective COX-2 inhibitors.

DETAILED DESCRIPTION OF THE INVENTION

The invention encompasses a process for synthesizing compounds represented by formula A:

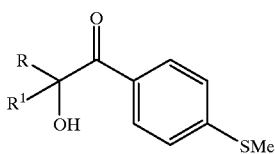

A wherein R and R¹ are $C_{1-6}$alkyl, comprising reacting a compound of formula B:

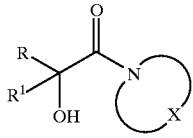

B wherein the group:

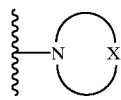

represents a 5 or 6-membered non-aromatic ring wherein X is selected from the group consisting of: C, N, O and S, with a lithiating agent and a compound of formula C:

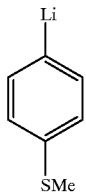

C in a substantially non-reactive solvent at reduced temperature to produce a compound of formula A.

In a preferred embodiment of the invention the lithiating agent is selected from the group consisting of: n-butyllithium, hexyllithium and phenyllithium.

In another embodiment the substantially non-reactive solvent is selected from the group consisting of: tetrahydrofuran, toluene, ethylene glycol dimethyl ether, t-butyl methyl ether and the like. Another embodiment of the invention encompasses a mixture of two or more of the aforesaid solvents.

In another embodiment of the invention the reduced temperature ranges from about −78° C. to about 0° C. In another preferred embodiment the reduced temperature is about −40° C.

A preferred embodiment of the invention is that wherein the reaction is quenched with an aqueous acid. Examples of quenching acids include: sulfuric acid, hydrochloric acid, citric acid and acetic acid.

Another embodiment of the invention is that wherein R is methyl and R¹ is ethyl.

Typically the compound of formula A consists of two stereoisomers, one stereoisomer in enantiomeric excess with respect to the other.

Another embodiment of the invention is that wherein the product yield of the compound of formula A is greater than about 90%.

In yet another embodiment, the following group of formula B:

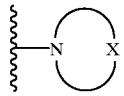

is selected from pyrrolidinyl, morpholinyl, piperidinyl and piperazinyl. More particularly, the group represents pyrrolidinyl.

A preferred embodiment of the invention encompasses the process wherein the compound of formula B is produced by reacting a compound of formula D:

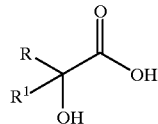

D wherein R and R¹ are $C_{1-6}$alkyl, with an activating agent in a substantially non-reactive solvent at reduced temperature and then with pyrrolidine at room temperature to produce a compound of formula B.

An example of an activating agent is carbonyldiimidazole.

Another embodiment is that wherein the substantially non-reactive solvent is selected from the group consisting of: tetrahydrofuran, toulene, isopropyl acetate, ethyl acetate, t-butlymethyl ether, ethylene glycol dimethyl ether and N,N-dimethylformamdide. Mixtures of two or more of the aforesaid solvents are also contemplated.

As used herein, the reduced temperature is in the range of about −25° C. to about 10° C. More particularly the reduced temperature is about 0° C.

A preferred embodiment is that wherein the product yield of the compound of formula B is greater than about 90%.

Another preferred embodiment is that wherein R is methyl and R¹ is ethyl.

A subclass of this class encompasses a process wherein the compound of formula D consists of one stereoisomer that is in enantiomeric excess with respect to the other.

A group of this subclass is a process wherein the compound of formula D is resolved by reacting the racemic mixture of the compound of formula D with a chiral amine resolving agent in a substantially non-reactive solvent.

Examples of substantially non-reactive solvent include those selected from the group consisting of: acetone, ethyl acetate, hexane and isopropyl acetate. Additionally mixtures of two or more of the aforesaid solvents are included.

A preferred embodiment is a process wherein the compound of formula D is resolved to an enantiomeric excess of about 98%.

In a more preferred embodiment the product yield for the resolution is greater than about 65%.

More particularly, the compound of formula D is resolved to about 98% enatiomeric excess and the yield is about 60–70%.

The invention is illustrated in connection with the following generic schemes A and B.

SCHEME A

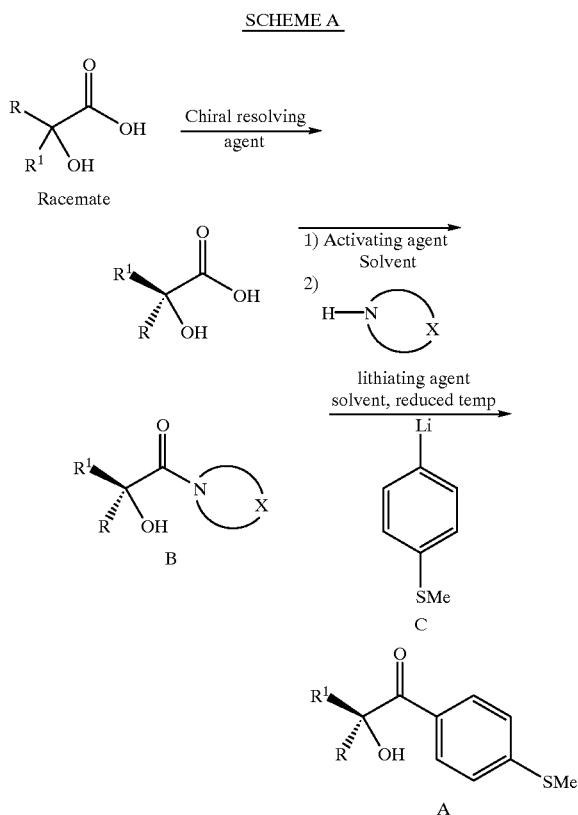

SCHEME B

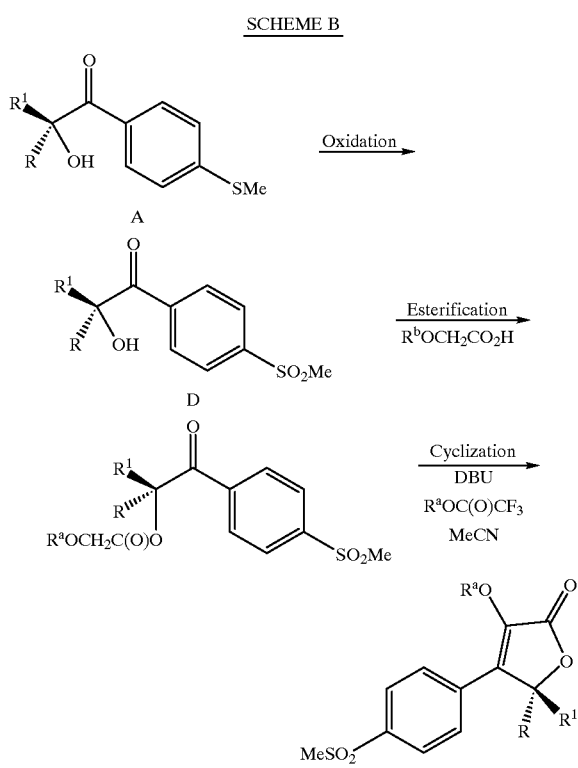

$R^a$ represents $C_{3-6}$ alkyl
$R^b$ represents $C_{2-6}$ alkyl

The racemic starting material is first separated into its diastereomers with a chiral amine resolving agent to provide the desired stereospecific hydroxy acid. Alternatively, the appropriate families of chiral amines may be used as described in T. Vries, et al., Angew Chem. Int. Ed. (1998) 37: 2349–2354.

Examples of chiral amine resolving agents can be selected from the group consisting of:

(1) (R)-(+)-1-(1-napthyl)ethylamine and
(2) (S)-(−)-1-(1-napthyl)ethylamine.

Illustrating this is a process wherein (S)-(+)-2-hydroxy-2-methyl butyric acid is resolved using (R)-(+)-1-(1-napthyl)ethylamine.

Another illustration is a process wherein (R)-(−)-2-hydroxy-2-methyl butyric acid is resolved using (S)-(−)-1-(1-napthyl)ethylamine.

The resolved hydroxy acid is then activated using an appropriate activating agent, in a substantially non-reactive solvent, at reduced temperature, and then combined with a cyclic amine, providing compound B. The cyclic amine serves as a leaving group in the next step, when is displaced via a lithiation reaction, producing compound A.

Compound A is oxidized to produce methyl sulfone D. A suitable oxidizing agent is Oxone®.

Methyl sulfone D is then subjected to esterification by reaction with a compound $R^aOCH_2CO_2H$, wherein $R^a$ represents a $C_{3-6}$ alkyl group. One example of a suitable esterification procedure involves the addition of the esterifying agent such as dicyclohexylcarbodiimide (DCC) to methyl sulfone D in the presence of an amine base, e.g., DABCO, in a solvent or solvent mixture at about 30–35° C. The ester is thereafter cyclized, and optionally deprotected, to provide compounds having COX-2 selective inhibitory activity.

For the purposes of this specification, the term "alkyl" means linear, branched or cyclic structures and combinations thereof, containing one to twenty carbon atoms. Examples of alkyl groups include methyl, ethyl, propyl, isopropyl, butyl, s- and t-butyl, pentyl, hexyl, heptyl, octyl, nonyl, undecyl, dodecyl, tridecyl, tetradecyl, pentadecyl, eicosyl, 3,7-diethyl-2,2-dimethyl-4-propylnonyl, and the like.

The term "substantially non-reactive solvent" includes tetrahydrofuran, toluene, acetone, ethyl acetate, hexane, isopropyl acetate, ethylene glycol dimethyl ether, t-butyl methyl ether and N,N-dimethylformamide.

The phrase "one stereoisomer that is in enantiomeric excess with respect to the other" means that the mixture contains over 50% of one stereoisomer and under 50% of the other. This phrase also is meant to include an enantiomerically pure compound consisting essentially of 100% of a stereoisomer and essentially 0% of the corresponding enantiomer.

The term "room temperature" means about 20° C.

The term "reduced temperature" is meant to include any temperature less than room temperature.

The term "lithiating agent" includes n-butyllithium, hexyllithium and phenyllithium.

The term "activating agent" means any compound that activates a particular site on any other compound for displacement by another group. An example is carbonyldiimidazole.

The term "chiral amine resolving agent" is meant to include any amine compound that when reacted with a mixture of enantiomers yields a mixture of one stereoisomer that is in enantiomeric excess with respect to the other and where such excess is greater than any excess of the original mixture. Examples include (R)-(+)-1-(1-napthyl)ethylamine and (S)-(−)-1-(1-napthyl)ethylamine.

The invention will now be illustrated by the following non-limiting examples:

PREPARATIVE EXAMPLE 1

Part A: Resolution

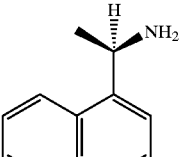

| Materials | mw | amount | mol | equiv |
|---|---|---|---|---|
| 2-Hydroxy-2-methylbutyric acid Aldrich (98%) | 118.13 | 2,500 g | 21.2 | 1.0 |
| (R)-(+)-1-(1-Naphthyl)ethylamine | 171.25 | 3,990 g | 23.3 | 1.1 |
| Acetone | | 19.0 L | | |

Under nitrogen, to a 50 L three-necked round bottom flask equipped with a mechanical stirrer, a nitrogen inlet and a thermocouple was charged with (R)-(+)-1-(1-naphthyl)ethylamine, acetone (19.0 L) at 10° C. 2-Hydroxy-2-methylbutyric acid was added as solid over 30 min. The mixture was aged at 9–11° C. for 72–96 hrs.

The mixture was warmed to 25° C. and the solid was isolated by filtration via an insulated sintered funnel. The wet cake was rinsed with cold acetone (0° C., 8 L). After the product was dried under reduced pressure it afforded 2,392 g of the salt (78% yield, >93% ee by LC). The product was recrystallized from acetone to give the salt in >98.5% ee and 70% yield.

Part B: Salt break. Recovery of acid and amine

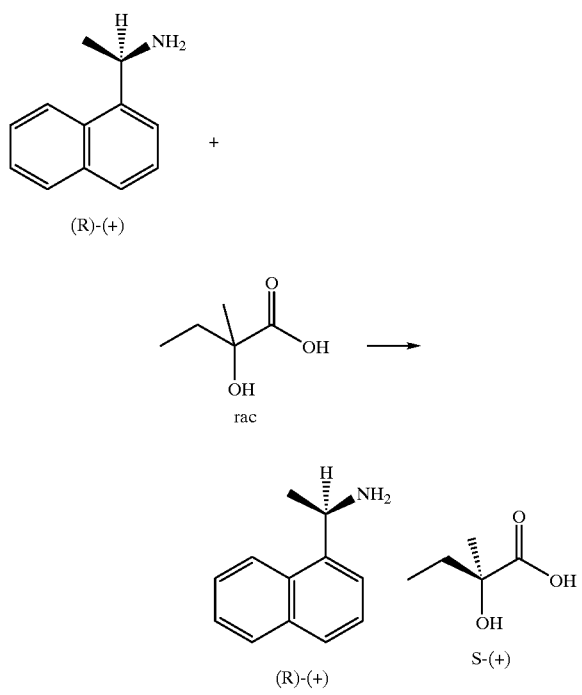

| Materials | mw | amount | mol. | equiv |
|---|---|---|---|---|
| The salt (ee of acid > 98.5%) | 289.38 | 1.985 kg | 6.86 | 1.0 |
| Dowex Resin 50WX4-200 (Aldrich) | | 13.3 kg | | |
| MeOH | | 66 L + 60 L | | |
| IPA | | 20 L + 30 L | | |
| Heptane | | 60 L + 4 L | | |

Under nitrogen, to a 50 L R.B. flask equipped with a mechanical stirrer, a nitrogen inlet and a thermocouple was charged with the salt from the previous step, freshly washed resin (13.3 kg, 66 L MeOH washed) and isopropanol (IPA) (20.0 L). The mixture was stirred for 2 h, the mixture was filtered and the resin was rinsed with IPA (30 L). The combined IPA solution was concentrated to approx. 5 L, heptane (60 L) was added and the mixture was re-concentrated to a volume of 30 L. The heptane solution was cooled to 0° C. The product was filtered, the wet cake was rinsed with heptane (0° C., 4 L) and the product was dried under reduced pressure, to give 794 g of (S)-(+)-2-hydroxy-2-methylbutyric acid (98% yield, overall yield for three steps 63.5%, ee >98.5%).

Under nitrogen, to a 50 L R.B. flask equipped with a mechanical stirrer, a nitrogen inlet and a thermocouple was charged with the recovered resin and 2M NH₃ in MeOH (30.0 L). (pH>8.5). The mixture was agitated for 3 hrs, and the resin was filtered and washed with MeOH (30 L). The resulting solution was concentrated to give crude (R)-(+)-1-(1-naphthyl)ethylamine (1,150 g, 98% yield).

EXAMPLE 1

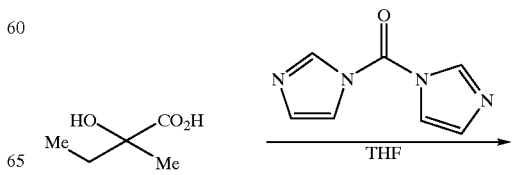

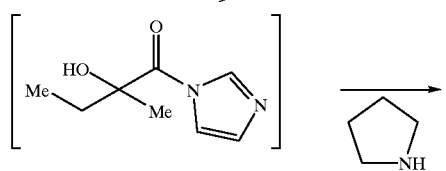

| Reagents | Amount |
|---|---|
| Hydroxy acid | 590 g (5 mol) |
| CDI | 818 g (5.05 mol, 1.01 eq) |
| THF | 8.7 L |
| Pyrrolidine | 711 g (10 mol, 2.0 eq) |
| Toluene | 36 L |
| 6 N HCl | 1.25 L, (7.5 mol, 1.5 eq) |

To carbonyldiimidazole (CDI) (818 g, 5.05 mol) in THF at 0° C. was added the hydroxy acid (580 g, 5 mol) over 30 min. The mixture was aged at 0° C. for 30 min and pyrrolidine (711 g, 10 mol) was added over 10 min, keeping the temperature below 25° C. The mixture was aged at room temperature for 30 min. The mixture was solvent switched to toluene (18 L), cooled to 0° C. and 6 N HCl was added portionwise, keeping the temperature below 25° C. The mixture was aged at room temperature for 30 min and the toluene layer was separated. The aq. layer was back extracted with toluene (2×9 L). Toluene layers were combined and concentrated to a solution (~3 mL/g of the amide B).

EXAMPLE 2

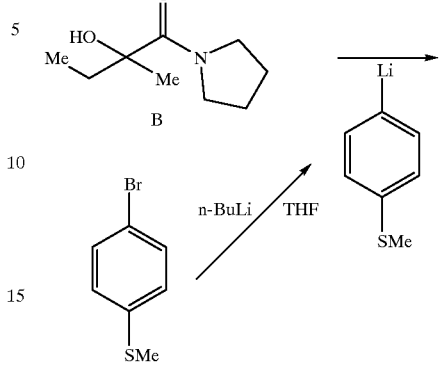

| Material | MW | mol | equiv. | amount |
|---|---|---|---|---|
| Amide (Crude) in 6 L Toluene | 169 | 9.52 | 1.0 | 1.609 kg |
| n-BuLi (1.6M in hexanes) | | 9.52 | 1.0 | 6.2 Lr |
| 4-bromothioanisole | 200 | 12.4 | 1.3 | 2.48 kg |
| n-BuLi (1.6M in hexanes) | | | 1.25 | 7.3 L |
| THF | | | | 51 L |
| Ph₃CH | | | 0.3 mol % | 6.9 g |
| IPAc | | | | 58 L |
| H₂SO₄ (conc.) | | | | 2.1 L |
| aq. NaHCO₃ | | | | 18 L (5 wt %) |

In a 20 L 4-necked flask equipped with N2 inlet, thermocouple, and overhead stirrer was charged the amide (solution in toluene), THF (850 mL) and Ph3CH (indicator). The solution was cooled to −65° C. and n-BuLi was added slowly (the endpoint was indicated by a colour change from yellow-brown to permanent red-brown).

In a 50 L 4 necked-RB flask, equipped with $N_2$ inlet. overhead stirrer, and thermocouple, was charged 4-bromothioanisole and THF (50 L). The solution was cooled to −62° C. and n-BuLi was added, over 1 h. The resulting heavy white slurry was aged at −50° C. to −60° C for 1 h. To this mixture was added the slurry of amide B lithium alkoxide, via cannula, and, and the reaction mixture was then warmed to 0° C. over 2 h.

Into a 125 L extractor was charged 16L deionized water and H₂SO₄ (2.1 L). The resulting solution was cooled to 10° C. The reaction mixture was transferred via cannula into the quench, (2 L THF rinse), with vigorous agitation. The layers were separated, and the aq. Layer was extracted with 30 L Toluene. The combined organics were washed with aq. NaHCO₃ (5 wt %, 18 L), and were then dried by concentration to approx 20 L. The assay yield of product was 2.29 kg (97%).

What is claimed is:

1. A process for synthesizing a compound represented by formula A:

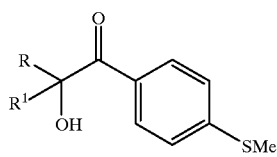

A wherein R and R¹ are $C_{1-6}$ alkyl,
comprising reacting a compound of formula B:

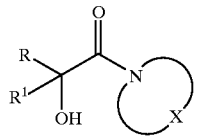

B wherein the group:

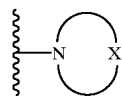

represents a 5 or 6-membered non-aromatic ring wherein X is selected from the group consisting of: C, N, O and S, with a lithiating agent and a compound of formula C:

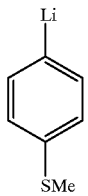

C in a substantially non-reactive solvent at reduced temperature to produce a compound of formula A.

2. A process according to claim 1 wherein the lithiating agent is selected from the group consisting of: n-butyllithium, hexyllithium and phenyllithium.

3. A process according to claim 1 wherein the substantially non-reactive solvent is selected from the group consisting of: tetrahydrofuran, toluene and ethylene glycol dimethyl ether.

4. A process according to claim 1 wherein the substantially non-reactive solvent is a mixture of two or more solvents selected from the group consisting of: tetrahydrofuran, toluene and ethylene glycol dimethyl ether.

5. A process according to claim 1 wherein the reduced temperature is from about −78° C. to about 0° C.

6. A process according to claim 1 wherein the reduced temperature is about −40° C.

7. A process according to claim 1 wherein the reaction is quenched with an acid.

8. A process according to claim 7 wherein the acid is selected from the group consisting of: sulfuric acid, hydrochloric acid, citric acid and acetic acid.

9. A process according to claim 1 wherein R is methyl and R¹ is ethyl.

10. A process according to claim 9 wherein the compound of formula A consists of a mixture of stereoisomers wherein one of the stereoisomers is in enantiomeric excess with respect to the other.

11. A process according to claim 1 wherein the product yield of the compound of formula A is greater than about 90%.

12. A process according to claim 1 wherein the following group of formula B:

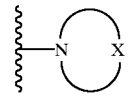

is selected from the group consisting of: pyrrolidinyl, morpholinyl, piperidinyl and piperazinyl.

13. A process according to claim 12 wherein the following group of formula B:

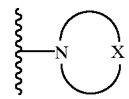

is pyrrolidinyl.

14. A process according to claim 1 wherein the compound of formula B is produced by reacting a compound of formula D:

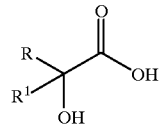

D wherein R and R¹ are $C_{1-6}$alkyl, with an activating agent in a substantially non-reactive solvent at reduced temperature and with pyrrolidine at room temperature to produce a compound of formula B.

15. A process according to claim 14 wherein the activating agent is carbonyldiimidazole.

16. A process according to claim 14 wherein the substantially non-reactive solvent is selected from the group consisting of: tetrahydrofuran, toluene, isopropyl acetate, ethyl acetate, t-butyl methyl ether, ethylene glycol dimethyl ether and N,N-dimethylformamide.

17. A process according to claim 14 wherein the substantially non-reactive solvent is a mixture of two or more solvents selected from the group consisting of: tetrahydrofuran, toluene, isopropyl acetate, ethyl acetate, t-butyl methyl ether, ethylene glycol dimethyl ether and N,N-dimethylformamide.

18. A process according to claim 14 wherein the reduced temperature is in the range of about −25° C. to about 10° C.

19. A process according to claim 14 wherein the reduced temperature is about 0° C.

20. A process according to claim 14 wherein R is methyl and R¹ is ethyl.

21. A process according to claim 20 wherein the compound of formula D consists of a mixture of stereoisomers wherein one of the stereoisomers is in enantiomeric excess with respect to the other.

22. A process according to claim 14 wherein the product yield of the compound of formula B is greater than about 90%.

23. A process in accordance with claim 21 wherein the compound of formula D is resolved by reacting a racemic mixture of the compound of formula D with a chiral amine resolving agent in a substantially non-reactive solvent.

24. A process according to claim 23 wherein the chiral amine resolving agent is selected from the group consisting of:
  (1) (R)-(+)-1-(1-napthyl)ethylamine and
  (2) (S)-(−)-1-(1-napthyl)ethylamine.

25. A process according to claim 24 wherein (S)-(+)-2-hydioxy-2-methyl butyric acid is obtained using (R)-(+)-1-(1-napthyl)ethylamine.

26. A process according to claim 24 wherein (R)-(−)-2-hydroxy-2-methyl butyric acid is obtained using (S)-(−)-1-(1-napthyl)ethylamine.

27. A process according to claim 23 wherein the substantially non-reactive solvent is selected from the group consisting of: acetone, ethyl acetate, hexane and isopropyl acetate.

28. A process according to claim 23 wherein the substantially non-reactive solvent is a mixture of two or more solvents selected from the group consisting of: acetone, ethyl acetate, hexane and isopropyl acetate.

29. A process according to claim 23 wherein the compound of formula D is resolved to an enantiomeric excess of about 98% with a product yield that is greater than about 65%.

* * * * *